US011674124B2

(12) United States Patent
Gil et al.

(10) Patent No.: US 11,674,124 B2
(45) Date of Patent: Jun. 13, 2023

(54) METHODS FOR PRODUCING MUTANT BACTERIOPHAGES FOR THE DETECTION OF LISTERIA

(71) Applicant: Laboratory Corporation of America Holdings, Burlington, NC (US)

(72) Inventors: Jose S. Gil, Winnetka, CA (US); Dwight L Anderson, Minneapolis, MN (US); Stephen Erickson, White Bear Township, MN (US); Minh Mindy Bao Nguyen, Shoreview, MN (US)

(73) Assignee: Laboratory Corporation of America Holdings, Burlington, NC (US)

( * ) Notice: Subject to any disclaimer, the term of this patent is extended or adjusted under 35 U.S.C. 154(b) by 105 days.

(21) Appl. No.: 16/905,607

(22) Filed: Jun. 18, 2020

(65) Prior Publication Data

US 2020/0399614 A1 Dec. 24, 2020

Related U.S. Application Data

(60) Provisional application No. 62/864,894, filed on Jun. 21, 2019.

(51) Int. Cl.

| | |
|---|---|
| ***A61K 31/7105*** | (2006.01) |
| ***A61K 35/15*** | (2015.01) |
| ***A61K 35/17*** | (2015.01) |
| ***A61K 39/00*** | (2006.01) |
| ***A61K 39/395*** | (2006.01) |
| ***C12N 7/00*** | (2006.01) |
| ***C12N 1/20*** | (2006.01) |
| *C12R 1/01* | (2006.01) |

(52) U.S. Cl.
CPC ............... *C12N 7/00* (2013.01); *C12N 1/205* (2021.05); *C12N 2795/00021* (2013.01); *C12N 2795/00051* (2013.01); *C12R 2001/01* (2021.05)

(58) Field of Classification Search
CPC .... A01N 63/60; A01N 63/50; A61K 2300/00; A61K 31/7105; A61K 31/711
See application file for complete search history.

(56) References Cited

U.S. PATENT DOCUMENTS

| | | | |
|---|---|---|---|
| 5,824,468 A | 10/1998 | Scherer et al. | |
| 5,837,465 A | 11/1998 | Squirrell et al. | |
| 6,225,066 B1 | 5/2001 | Jacobs, Jr. et al. | |
| 7,252,996 B2 | 8/2007 | Boccaccio et al. | |
| 8,318,474 B1 | 11/2012 | Smolke et al. | |
| 8,557,970 B2 | 10/2013 | Encell et al. | |
| 8,865,399 B2 | 10/2014 | Schofield | |
| 9,482,668 B2 | 11/2016 | Anderson et al. | |
| 9,988,608 B1 * | 6/2018 | Crown ................... | C12N 15/01 |
| 10,519,483 B2 | 12/2019 | Anderson et al. | |
| 2002/0160525 A1 | 6/2002 | Takahata et al. | |
| 2004/0137430 A1 | 7/2004 | Anderson et al. | |
| 2005/0003346 A1 | 1/2005 | Voorhees et al. | |
| 2009/0155768 A1 | 6/2009 | Scholl et al. | |
| 2009/0246752 A1 | 10/2009 | Voorhees et al. | |
| 2010/0291541 A1 | 11/2010 | Evoy et al. | |
| 2011/0201013 A1 | 8/2011 | Moore | |
| 2013/0122549 A1 | 5/2013 | Lu et al. | |
| 2013/0216997 A1 | 8/2013 | Anderson et al. | |

FOREIGN PATENT DOCUMENTS

| | | |
|---|---|---|
| EP | 0743366 | 11/1996 |
| JP | 11337553 A | 12/1999 |
| JP | 2002-160525 A | 6/2002 |
| JP | 2005-524394 A | 8/2005 |
| JP | 2006-510002 A | 3/2006 |
| JP | 2007-523628 A | 8/2007 |
| JP | 2010-507371 A | 3/2010 |
| JP | 2010-088456 A | 4/2010 |
| WO | 99/45396 | 9/1999 |
| WO | 2003/035889 A2 | 5/2003 |
| WO | 2005/001475 A2 | 1/2005 |
| WO | 2007/055737 | 5/2007 |
| WO | 2008/124119 A1 | 10/2008 |
| WO | 2013/126584 A1 | 8/2013 |
| WO | 2015/126966 A2 | 8/2015 |
| WO | 2017/127434 A1 | 7/2017 |

OTHER PUBLICATIONS

Jensen, E. et al., "Prevalence of Broad-Host-Range Lytic Bacteriophages of *Sphaerotilus natans, Escherichia coli*, and *Pseudomonas aeruginosa*," Appl. Environ. Microbiol. 64(2):575-580 (1998).
Kelly, D. et al., "Development of a Broad-Host-Range Phage Cocktail for Biocontrol," Bioengineered Bugs 2(1):31-37 (2011).
Xie, Y. et al., "Development and Validation of a Microtiter Plate-Based Assay for Determination of Bacteriophage Host Range and Virulence," Viruses 10(4):189 (2018) 16 pages.
PCT/US2020/038501, International Preliminary Report on Patentability, dated Dec. 30, 2021, 9 pages.
PCT/US2020/038501, International Search Report and Written Opinion, dated Nov. 13, 2020, 14 pages.
U.S. Appl. No. 14/625,481, "Final Office Action", dated Jun. 13, 2019, 11 pages.
U.S. Appl. No. 13/773,339, Final Office Action, dated Jun. 9, 2015.
AU 2013222411, First Examination Report, dated Nov. 2, 2017, 4 pages.

(Continued)

*Primary Examiner* — Barry A Chestnut
(74) *Attorney, Agent, or Firm* — Kilpatrick Townsend & Stockton LLP

(57) ABSTRACT

Disclosed herein are methods for the production of mutant bacteriophages with altered host range. Additionally, disclosed herein are methods and systems for rapid detection of microorganisms such as *Listeria* spp. in a sample. A genetically modified bacteriophage is also disclosed which comprises an indicator gene in the late gene region. The specificity of the bacteriophage, such as *Listeria*-specific bacteriophage, allows detection of a specific microorganism, such as *Listeria* spp. and an indicator signal may be amplified to optimize assay sensitivity.

29 Claims, No Drawings

(56) References Cited

OTHER PUBLICATIONS

Bague, J., Detection of Recombinant Human Erythropoietin and Analogues through Immunorecognition and N-Giycolyi-Neuraminic Acid Identification, Doctoral Thesis Pompeu Fabra University, Department of Experimental and Health Sciences, 2011. Retrieved from http//www.tesisenred.net/bitstream/handel/10803/31960/tjm.pdf?sequence=1 as available via the Internet and printed Mar. 27, 2013, 41 pages.
Billard and DuBow. Bioluminescence-based assays for detection and characterization of bacteria and chemicals in clinical laboratories. Clinical Biochemistry, Feb. 1998;31(1):1-14. (Year: 1998).
CA 2,865,308, "Office Action", dated Jun. 4, 2019, 3 pages.
CN 201710263366.1, "Office Action", dated Jul. 31, 2019, 10 pages.
Edgar, R. et al., High-sensitivity bacterial detection using biotin-tagged phage and quantum-dot nanocomplexes, Proc. Natl. Acad. Sci. USA, 2006, 103(13):4841-5. Epub, Mar. 28, 2006, 5 pages.
Elena et al., "Expression of codon optimized genes in microbial systems: current industrial applications and perspectives. Art. 21", Frontiers in Microbiology, vol. 5, Feb. 1, 2014, pp. 1-8.
EP 19152164.0, "Extended European Search Report", dated Jul. 10, 2019, 6 pages.
EP 17703002.0, "Office Action," dated Dec. 18, 2019, 5 pages.
EP 13751965.8, "Extended European Search Report", dated Sep. 30, 2015, 7 pages.
EP 13751965.8, Communication Pursuant to Article 94(3) EPC, dated Apr. 11, 2017, 6 pages.
EP 13751965.8, Communication Pursuant to Article 94(3) EPC, dated Jan. 30, 2018, 6 pages.
EP 13751965.8, Office Action, dated Jan. 30, 2018, 6 pages.
Goodridge, L. et al., Reporter bacteriophage assays as a means to detect foodborne pathogenic bacteria, Food Research International, 2002, 35:863-870.
Hagens, S. et al., Reporter bacteriophage A511::celB transduces a hyperthermostable glycosidase from Pyrococcus furiosus for rapid and simple detection of viable Listeria cells, Bacteriophage, 2011, 1(3):143-151. Epub May 1, 2011.
Hagens, S. et al., "Bacteriophage for Biocontrol of Foodborne Pathogens: Calculations and Considerations", Current Pharmaceutical Biotechnology, vol. 11, No. 1, Feb. 10, 2010, pp. 58-68, 11 pages.
He, Y. et al., "Monoclonal antibodies for detection of the H7 antigen of *Escherichia coli*", Applied Environ Microbiology, 1996, 62(9):3325-32.
Inouye, S. et al., Overexpression, purification and characterization of the catalytic component of Oplophorus luciferase in the deep-sea shrimp, Oplophorus gracilirostris. Protein Expression & Purification, 2007, 56(2):261-8, 8 pages.
International Search Report for International Patent Application No. PCT/US2017/013955, dated May 15, 2017.
Jacobs et al., Science, 1993, 260:819-822 (Year: 1993).
JP 2014-558827, Reasons for Rejection, dated Nov. 1, 2016, 9 pages.
JP 2017-16551, Reasons for Rejection, dated Jan. 19, 2018, 5 pages.
JP 2014-558827, Notice of Reasons for Rejection, dated Nov. 1, 2016.
JP 2017-016551, "Office Action", dated Dec. 21, 2018, 12 pages.
Kodikara, C. et al., Near on-line detection of enteric bacteria using lux recombinant bacteriophage, FEMS Microbiology Letters, 1991, 67(3):261-5, 5 pages.
Kutter, et al., "Characterization of a Vil-like Phage Specific to *Escherichia coli* O157:H7," Virology J. 8:430 (2011).
Loessner et al., Applied And Environmental Microbiology, Apr. 1996, 62(4):1133-1140. (Year: 1996).
Loessener, M. et al., "Construction Of Luciferase Reporter Bacteriophage A511::LuxAB for Rapid and Sensitive Detection of Viable Listeria Cells", Applied and Environmental Microbiology, vol. 62, No. 4, Apr. 1996, pp. 1133-1140, 8 pages.
Loessener, M. et al., Evaluation of luciferase reporter bacteriophage A511::luxAB for detection of Listeria monocytogenes in contaminated foods, Appl. Environ. Microbiol., 1997, 63(8):2961-5, 5 pages.
Lu, T. et al., "Advancing bacteriophage-based microbial diagnostics with synthetic biology", Trends in Biotechnology, 2013, 31(6):325-7, 3 pages.
Macdonald and Mosig. Regulation of a new bacteriophage T4 gene, 69, that spans an origin of DNA replication. The EMBO Journal vol. 3 No. 12 pp. 2863-2871, 1984.
MX MX/A/2014/010069, Office Action, dated Apr. 25, 2017, 2 pages.
Miyanaga et al. "Detection of *Escherichia coli* in the sewage influent by fluorescent labeled T4 phage", Biochemical Engineering Journal, vol. 29, Issues 1-2, Apr. 1, 2006, pp. 119-124, 6 pages.
Noguera, P. et al., "Carbon nanoparticles in lateral flow methods to detect genes encoding virulence factors of Shiga toxin-producing", Anal Bioanal. Chem. 2011, 399(2): 831-838.
Non-Final Office Action dated Oct. 31, 2014 for U.S. Appl. No. 13/773,339.
Patent Cooperation Treaty, International Search Report and Written Opinion, International Application No. PCT/US13/27155, dated May 6, 2013.
Patent Cooperation Treaty, International Search Report and Written Opinion, International Application No. PCT/US2015/016415, dated Jun. 22, 2015.
PCT/US2017/013955, "International Preliminary Report on Patentability", dated Aug. 2, 2018, 9 pages.
PCT/US2017/013955, "International Search Report and Written Opinion", dated May 15, 2017, 16 pages.
PCT/US2017/013955, "Invitation to Pay Additional Fees and Partial Search Report", dated Mar. 20, 2017, 7 pages.
Rees, C. et al., Chapter 14—"The Use of Phage Detection, Antibiotic Sensitivity Testing and Enumeration", InTech In: Understanding Tuberculosis—Global Experiences and Innovative Approaches to the Diagnosis, Feb. 15, 2012, 14 pages. Edited by Dr. Pere-Joan Cardona.
Rees C. et al., The Use of Phage of Diagnostic Systems, Division of Food Sciences, School of Biosciences, University of Nottingham, Sutton Bonington Campus Loughborough, Leicestershire LE12 5RD, UK; The Bacteriophages, 2nd edition (2006) Richard Calendar—Oxford University Press, 15 pages.
Schofield, D. et al., Phage-based platforms for the clinical detection of human bacterial pathogens, Bacteriophage, 2012, 2(2):105-283, 17 pages.
Smietana, M. et al., "Detection of bacteria using bacteriophages as recognition elements immobilized on long-period fiber gratings", Optics Express, vol. 19, No. 9, Apr. 25, 2011, pp. 7971-7978, 8 pages.
State Intellectual Property Office of the Peoples Republic of China Application No. 201380019483.3, Office Action dated Jul. 7, 2015, 14 pages.
State Intellectual Property Office of the Peoples Republic of China, Application No. 201380019483.3, Office Action dated Feb. 4, 2016, 11 pages.
State Intellectual Property Office of the Peoples Republic of China Application No. 201380019483.3, Office Action dated Jul. 18, 2016, 9 pages.
State Intellectual Property Office of the Peoples Republic of China, Notification of the Third Office Action, Application No. 201380019483 dated Jul. 18, 2016.
Tanji et al., "*Escherichia coli* Detection by GFP-labeled Lysozyme-inactivated T4 Bacteriophage", Journal of Biotechnology, vol. 114, No. 1-2, Oct. 19, 2004, pp. 11-20, 10 pages.
Ulitzur, N. et al., "New Rapid and Simple Methods for Detection of Bacteria and Determination of Their Antibiotic Susceptibility by Using Phage Mutants", Applied and Environmental Microbiology, vol. 72, No. 12, Dec. 1, 2006, pp. 7455-7459.
U.S. Appl. No. 13/773,339, Non-Final Office Action dated Mar. 3, 2016, 26 pages.
U.S. Appl. No. 14/625,481, Non-Final Office Action dated Oct. 18, 2016, 10 pages.

(56) References Cited

OTHER PUBLICATIONS

U.S. Appl. No. 14/625,481, Non-Final Office Action dated Apr. 26, 2017, 9 pages.
U.S. Appl. No. 14/625,481, Non-Final Office Action dated Jan. 25, 2018, 8 pages.
U.S. Appl. No. 15/263,619, "Non-Final Office Action", dated Mar. 26, 2018, 19 pages.
U.S. Appl. No. 15/263,619, "Non-Final Office Action", dated May 13, 2019, 21 pages.
U.S. Appl. No. 15/263,619, "Final Office Action", dated Feb. 12, 2020, 27 pages.
Wu, L. et al., Trace detection of specific viable bacteria using tetracysteine-tagged bacteriophages, Anal Chem. 2014, 86(1):907-12. Epub Dec. 10, 2013, 6 pages.
Burrows, B. et al., "Directed in Vitro Evolution of Therapeutic Bacteriophages: The Appelmans Protocol," Viruses 11:241 (2019), 15 pages.
CA 3,140,294, Office Action, dated Jan. 3, 2023, 4 pages.

* cited by examiner

METHODS FOR PRODUCING MUTANT BACTERIOPHAGES FOR THE DETECTION OF LISTERIA

CROSS REFERENCE TO RELATED APPLICATIONS

This application claims priority to U.S. Provisional Patent Application No. 62/864,894 filed Jun. 21, 2019. The disclosures of U.S. Application No. 62/864,894 and Ser. No. 16/776,417 are hereby incorporated by reference in their entirety herein.

FIELD OF THE INVENTION

This invention relates to methods for the production of bacteriophage and the resultant bacteriophage.

BACKGROUND

There is a strong interest in improving sensitivity for detection of bacteria, viruses, and other microorganisms in biological, food, water, and clinical samples. Microbial pathogens can cause substantial morbidity among humans and domestic animals, as well as immense economic loss. Also, detection of microorganisms is a high priority for the Food and Drug Administration (FDA) and Centers for Disease Control (CDC), as well as the United States Department of Agriculture (USDA), given outbreaks of life-threatening or fatal illness caused by ingestion of food contaminated with certain microorganisms, e.g., *Listeria* spp., *Salmonella* spp., or *Staphylococcus* spp.

Traditional microbiological tests for the detection of bacteria rely on non-selective and selective enrichment cultures followed by plating on selective media and further testing to confirm suspect colonies. Such procedures can require several days. A variety of rapid methods have been investigated and introduced into practice to reduce the time requirement. However, these methods have drawbacks. For example, techniques involving direct immunoassays or gene probes generally require an overnight enrichment step in order to obtain adequate sensitivity. Polymerase chain reaction (PCR) tests also include an amplification step and therefore are capable of both very high sensitivity and selectivity; however, the sample size that can be economically subjected to PCR testing is limited. With dilute bacterial suspensions, most small sub samples will be free of cells and therefore purification and/or lengthy enrichment steps are still required.

The time required for traditional biological enrichment is dictated by the growth rate of the target bacterial population of the sample, by the effect of the sample matrix, and by the required sensitivity. In practice, most high sensitivity methods employ an overnight incubation and take about 24 hours overall. Due to the time required for cultivation, these methods can take up to three days, depending upon the organism to be identified and the source of the sample. This lag time is generally unsuitable as the contaminated food, water, or other product may have already made its way into livestock or humans. In addition, increases in antibiotic-resistant bacteria and biodefense considerations make rapid identification of bacterial pathogens in water, food and clinical samples critical priorities worldwide.

Bacteriophage (phage) can be used to detect pathogenic bacteria in food, environmental, and clinical samples due to their narrow range of host specificity. The narrow host-range of phage can be used to detect potentially pathogenic bacteria while excluding detection of non-harmful bacteria. However, phage can be too specific to detect each serotype or species of potentially harmful bacteria present in a sample. Detection of bacteria of interest in a sample can require the use of phage cocktails. Thus, expanding the host-range of a phage specific for a particular host to include a new target host of interest can be advantageous.

Therefore, there is a need for methods of producing bacteriophages with expanded host-range and bacteriophages with expanded host-ranges.

SUMMARY

Embodiments of the disclosure comprise methods of producing mutant bacteriophages (phages) with an expanded host-range and the resulting phages. The present disclosure may be embodied in a variety of ways.

In one aspect, the present disclosure is directed to a method of producing a mutant bacteriophage with an expanded host-range. In some embodiments, the method comprises (i) preparing a series of first co-culture mixtures of varying ratios comprising a host bacterial strain and a target-host bacterial strain; (ii) adding a phage strain to each of the first co-culture mixtures; (iii) incubating the first co-culture mixtures and the phage strain under bacterial culture conditions; (iv) collecting a phage lysate from each of the plurality of first-co-cultures; (v) pooling the phage lysates from each of the plurality of first co-cultures; (vi) assaying phage lysates to determine if the bacteria host-range has expanded; and (vii) isolating a mutant phage with expanded host-range.

In another aspect, the present disclosure is directed to the resulting mutant bacteriophage with expanded host-range, wherein the mutant bacteriophage is capable of infecting a host bacterial strain and a target-host bacterial strain.

In other instances, it is advantageous to utilize a bacteriophage with narrow host range. Thus in another aspect, the present disclosure is directed to a method of producing a mutant bacteriophage with a reduced host-range. In some embodiments, the method comprises (i) mutating a gene encoding a tail spike protein of a bacteriophage (ii) producing progeny phage lysates from the mutated bacteriophage; (iii) assaying phage lysates to determine if the bacteria host-range has reduced; and (iv) isolating a mutant phage with reduced host-range.

In yet another aspect, the present disclosure is directed to a recombinant bacteriophage comprising an indicator gene inserted into a late gene region of a mutant bacteriophage with expanded host-range genome. In some embodiments the recombinant bacteriophage is a genetically modified *Listeria*-specific bacteriophage genome. In certain embodiments the recombinant bacteriophage comprises a genetically modified bacteriophage genome derived from a bacteriophage that specifically recognizes *Listeria* spp. In some embodiments, the bacteriophage used to prepare the recombinant bacteriophage specifically infects one or more *Listeria* spp. In an embodiment, the recombinant bacteriophage can distinguish a host bacterial strain and a target-host bacterial strain in the presence of other types of bacteria.

Also disclosed herein are methods for preparing a recombinant indicator bacteriophage. Some embodiments include selecting a wild-type bacteriophage that specifically infects a target pathogenic bacterium; preparing a homologous recombination plasmid/vector comprising an indicator gene; transforming the homologous recombination plasmid/vector into target pathogenic bacteria; infecting the transformed target pathogenic bacteria with the selected wild-type bacteriophage, thereby allowing homologous recombination to occur between the plasmid/vector and the bacteriophage genome; and isolating a particular clone of recombinant bacteriophage. In some embodiments the selected wild-type bacteriophage is a *Listeria*-specific bacteriophage. In some embodiments, the selected wild-type bacteriophage is a myovirus, such as T4, T4likevirus, *Listeria* phage LMTA-94, P 100virus or Vil-like. In some embodiments, the selected wild-type bacteriophage infects *Listeria* spp. In other embodiments, the selected wild-type bacteriophage is a podovirus, such as T7-likevirus, or Sp6-like virus. In other embodiments, the selected wild-type bacteriophage is LMA4 and LMA8. LMA4 and LMA8 are Myoviruses, likely in the genus P100virus.

In some embodiments, the invention comprises a method for detecting a microorganism of interest in a sample comprising the steps of incubating the sample with a recombinant bacteriophage that infects the microorganism of interest, wherein the recombinant bacteriophage comprises an indicator gene inserted into a late gene region of the bacteriophage such that expression of the indicator gene during bacteriophage replication following infection of host bacteria results in a soluble indicator protein product, and detecting the indicator protein product, wherein positive detection of the indicator protein product indicates that the microorganism of interest is present in the sample.

DETAILED DESCRIPTION OF THE INVENTION

Disclosed herein are methods for producing bacteriophage with an expanded host-range and the resulting mutant bacteriophage, which can be used for the detection of a microorganism of interest, such as *Listeria* spp., in test samples (e.g., biological, food, water, and environmental samples). Detection can be achieved in a shorter timeframe than was previously thought possible using genetically modified infectious agents in assays performed without culturing for enrichment, or in some embodiments with minimal incubation times during which microorganisms could potentially multiply.

In some aspects, the present disclosure is directed to a method for detecting a microorganism of interest. The method may use an infectious agent for detection of the microorganism of interest such as *Listeria* spp. For example, in certain embodiments, the microorganism of interest is *Listeria* spp. and the infectious agent is a bacteriophage that specifically infects *Listeria* spp. In some embodiments, the bacteriophage has been mutated to have an expanded host-range and is capable of infecting multiple serotypes of *Listeria monocytogenes*. Thus, in certain embodiments, the method may comprise detection of a bacterium of interest in a sample by incubating the sample with a recombinant mutant bacteriophage that infects the bacterium of interest. In certain embodiments, the recombinant mutant bacteriophage comprises an indicator gene. The indicator gene may, in certain embodiments, be inserted into a late gene region of the bacteriophage such that expression of the indicator gene during bacteriophage replication following infection of host bacteria results in production of an indicator protein product. The method may comprise detecting the indicator protein product, wherein positive detection of the indicator protein product indicates that the bacterium of interest is present in the sample. In some embodiment the indicator protein is soluble.

Embodiments of the methods and systems of the invention can be applied to detection and quantification of a variety of microorganisms (e.g., bacteria) in a variety of circumstances, including but not limited to detection of pathogens from food, water, and commercial samples. The methods of the present invention provide high detection sensitivity and specificity rapidly. In some embodiments detection is possible within a single replication cycle of the bacteriophage, which is unexpected.

Definitions

Unless otherwise defined herein, scientific and technical terms used in connection with the present invention shall have the meanings that are commonly understood by those of ordinary skill in the art. Further, unless otherwise required by context, singular terms shall include pluralities and plural terms shall include the singular. Generally, nomenclatures used in connection with, and techniques of, cell and tissue culture, molecular biology, immunology, microbiology, genetics and protein and nucleic acid chemistry and hybridization described herein are those well-known and commonly used in the art. Known methods and techniques are generally performed according to conventional methods well known in the art and as described in various general and more specific references that are discussed throughout the present specification unless otherwise indicated. Enzymatic reactions and purification techniques are performed according to manufacturer's specifications, as commonly accomplished in the art or as described herein. The nomenclatures used in connection with the laboratory procedures and techniques described herein are those well-known and commonly used in the art.

The following terms, unless otherwise indicated, shall be understood to have the following meanings:

As used herein, the terms "a", "an", and "the" can refer to one or more unless specifically noted otherwise.

The use of the term "or" is used to mean "and/or" unless explicitly indicated to refer to alternatives only or the alternatives are mutually exclusive, although the disclosure supports a definition that refers to only alternatives and "and/or." As used herein "another" can mean at least a second or more.

Throughout this application, the term "about" is used to indicate that a value includes the inherent variation of error for the device, the method being employed to determine the value, or the variation that exists among samples.

The term "solid support" or "support" means a structure that provides a substrate and/or surface onto which biomolecules may be bound. For example, a solid support may be an assay well (i.e., such as a microtiter plate or multi-well plate), or the solid support may be a location on a filter, an array, or a mobile support, such as a bead or a membrane (e.g., a filter plate, latex particles, paramagnetic particles, or lateral flow strip).

The term "binding agent" refers to a molecule that can specifically and selectively bind to a second (i.e., different) molecule of interest. The interaction may be non-covalent, for example, as a result of hydrogen bonding, van der Waals interactions, or electrostatic or hydrophobic interactions, or it may be covalent. The term "soluble binding agent" refers to a binding agent that is not associated with (i.e., covalently or non-covalently bound) to a solid support.

As used herein, an "analyte" refers to a molecule, compound or cell that is being measured. The analyte of interest may, in certain embodiments, interact with a binding agent. As described herein, the term "analyte" may refer to a protein or peptide of interest. An analyte may be an agonist, an antagonist, or a modulator. Or, an analyte may not have a biological effect. Analytes may include small molecules, sugars, oligosaccharides, lipids, peptides, peptidomimetics, organic compounds and the like.

The term "detectable moiety" or "detectable biomolecule" or "reporter" or "indicator" or "indicator moiety" refers to a molecule that can be measured in a quantitative assay. For example, an indicator moiety may comprise an enzyme that may be used to convert a substrate to a product that can be measured. An indicator moiety may be an enzyme that catalyzes a reaction that generates bioluminescent emissions (e.g., luciferase). Or, an indicator moiety may be a radioisotope that can be quantified. Or, an indicator moiety may be a fluorophore. Or, other detectable molecules may be used.

As used herein, "bacteriophage" or "phage" includes one or more of a plurality of bacterial viruses. In this disclosure, the terms "bacteriophage" and "phage" include viruses such as mycobacteriophage (such as for TB and paraTB), mycophage (such as for fungi), mycoplasma phage, and any other term that refers to a virus that can invade living bacteria, fungi, mycoplasma, protozoa, yeasts, and other microscopic living organisms and uses them to replicate itself. Here, "microscopic" means that the largest dimension is one millimeter or less. Bacteriophages are viruses that have evolved in nature to use bacteria as a means of replicating themselves. A phage does this by attaching itself to a bacterium and injecting its DNA (or RNA) into that bacterium, and inducing it to replicate the phage hundreds or even thousands of times. This is referred to as phage amplification.

As used herein, "late gene region" refers to a region of a viral genome that is transcribed late in the viral life cycle. The late gene region typically includes the most abundantly expressed genes (e.g., structural proteins assembled into the bacteriophage particle). Late genes are synonymous with class III genes and include genes with structure and assembly functions. For example, the late genes (synonymous with class III,) are transcribed in phage T7, e.g., from 8 minutes after infection until lysis, class I (e.g., RNA polymerase) is early from 4-8 minutes, and class II from 6-15 minutes, so there is overlap in timing of II and III. A late promoter is one that is naturally located and active in such a late gene region.

As used herein, "culturing for enrichment" refers to traditional culturing, such as incubation in media favorable to propagation of microorganisms, and should not be confused with other possible uses of the word "enrichment," such as enrichment by removing the liquid component of a sample to concentrate the microorganism contained therein, or other forms of enrichment that do not include traditional facilitation of microorganism propagation. Culturing for enrichment for periods of time may be employed in some embodiments of methods described herein.

As used herein, "host range" refers to the number of host species used by a pathogen. Host range describes the breadth of organisms a bacteriophage is capable of infecting, with limits on host range stemming from bacteriophage, host, or environmental characteristics.

As used herein "recombinant" refers to genetic (i.e., nucleic acid) modifications as usually performed in a laboratory to bring together genetic material that would not otherwise be found. This term is used interchangeably with the term "modified" herein.

As used herein "RLU" refers to relative light units as measured by a luminometer (e.g., GLOMAX® 96) or similar instrument that detects light. For example, the detection of the reaction between luciferase and appropriate substrate (e.g., NANOLUC® with NANO-GLO®) is often reported in RLU detected.

As used herein "time to results" refers to the total amount of time from beginning of sample incubation to generated result. Time to results does not include any confirmatory testing time. Data collection can be done at any time after a result has been generated.

Production of Mutant Bacteriophage

Embodiments of methods of producing mutant bacteriophages with expanded host-range begin with selection of a bacteriophage for genetic modification. Some bacteriophage are highly specific for a target bacterium. This presents an opportunity for highly specific detection. In some instances, it is advantageous to expand the host-range of a highly specific phage to allow detection of multiple strains of potentially harmful bacteria in a single assay.

The host range of a bacteriophage is considered to be the breadth (i.e., genera, species, or strains) of bacteria that the bacteriophage is able to productively infect. The host range of some bacteriophages is rather narrow, only having the ability to infect a few strains within the same species. Other phages can infect many species of bacteria, sometimes across different genera. However, most bacteriophages are believed to have a relatively narrow host range. This may be due in part to the specificity of phages' host binding proteins, biochemical interactions during infection, presence of related prophages or particular plasmids, and bacterial phage-resistance mechanisms.

In some instances, it is advantageous to utilize a phage with a very broad host range. Thus in one aspect, the present disclosure is directed to a method of producing a mutant bacteriophage with an expanded host-range. In some embodiments, the method comprises (i) preparing a series of first co-culture mixtures of varying ratios comprising a host bacterial strain and a target-host bacterial strain; (ii) adding a phage strain to each of the first co-culture mixtures; (iii) incubating the first co-culture mixtures and the phage strain under bacterial culture conditions; (iv) collecting a phage lysate from each of the plurality of first-co-cultures; (v) pooling the phage lysates from each of the plurality of first co-cultures; (vi) assaying phage lysates to determine if the bacteria host-range has expanded; and (vii) isolating a mutant phage with expanded host-range.

In other instances, it is advantageous to utilize a bacteriophage with narrow host range. Thus in another aspect, the present disclosure is directed to a method of producing a mutant bacteriophage with a reduced host-range. In some embodiments, the method comprises (i) mutating a gene encoding a tail spike protein of a bacteriophage (ii) producing progeny phage lysates from the mutated bacteriophage; (iii) assaying phage lysates to determine if the bacteria host-range has reduced; and (iv) isolating a mutant phage with reduced host-range.

In some embodiments the selected wild-type bacteriophage is a *Listeria*-specific bacteriophage. In certain embodiments, the selected wild-type bacteriophage is from the Caudovirales order of phages. Caudovirales are an order of tailed bacteriophages with double-stranded DNA (dsDNA) genomes. Each virion of the Caudovirales order has an icosahedral head that contains the viral genome and a flexible tail. The Caudovirales order comprises five bacteriophage families: Myoviridae (long contractile tails), Siphoviridae (long non-contractile tails), Podoviridae (short non-contractile tails), Ackermannviridae, and Herelleviridae. The term myovirus can be used to describe any bacteriophage with an icosahedral head and a long contractile tail, which encompasses bacteriophages within both the Myoviridae and Herelleviridae families. In some embodiments, the selected wild-type bacteriophage is a member of the Myoviridae family such as, *Listeria* phage B054, *Listeria* phage LipZ5, *Listeria* phage PSU-VKH-LP041, and *Listeria* phage WIL-2. In other embodiments, the selected wild-type bacteriophage is a member of the family Herelleviridae. The genus *Pecentumvirus*, under the family Herelleviridae includes bacteriophages such as *Listeria* phage LMSP-25, *Listeria* phage LMTA-148, *Listeria* phage LMTA-34, *Listeria* phage LP-048, *Listeria* phage LP-064, *Listeria* phage LP-083-2, *Listeria* phage LP-125, *Listeria* virus P100, *Listeria* phage List-36, *Listeria* phage WIL-1, *Listeria* phage vB_LmoM_AG20, and *Listeria* virus A511. LMA4 and LMA8 are also likely in the genus *Pecentumvirus*, under the family Herelleviridae. In other embodiments, the selected wild-type bacteriophage is LMA4 or LMA8. In certain instances the selected wild-type bacteriophage is LP-ES3A, which is derived from A511 but has been adapted to be capable of infecting serotype 3A of *Listeria monocytogenes*. In still other embodiments, the selected wild-type bacteriophage is a member of the family Ackermannviridae. In still other embodiments, the selected wild-type bacteriophage is a member of the family Siphoviridae, which includes *Listeria* phages A006, A118, A500, B025, LP-026, LP-030-2, LP-030-3, LP-037, LP-101, LP-110, LP-114, P35, P40, P70, PSA, vB_LmoS_188, and vB_Lmos_293. In other embodiments, the selected wild-type bacteriophage is LP-ES1. LP-ES1 is also likely in the genus *Homburgvirus*, under the family Siphoviridae.

In some embodiments, the method of producing a mutant bacteriophage with an expanded host-range comprises identifying and selecting a bacteriophage that is specific for a bacteria of interest. In some embodiments, the bacteria of interest is a potentially harmful bacteria. In further embodiments, the selected bacteriophage is capable of infecting a host bacterial strain but is unable of infecting a target-host bacterial strain. A host bacterial strain is any bacterial strain that a selected phage is capable of infecting. A target-host bacterial strain is any bacterial strain that a selected phage is not capable of infecting. In some embodiments, the selected phage is mutated to be capable of infecting a target-host bacterial strain.

In other embodiments, the methods of producing a mutant bacteriophage with a reduced host-range comprises identifying and selecting a bacteriophage that is specific for a bacteria of interest. In some embodiments, the bacteria of interest is a potentially harmful bacteria. In further embodiments, the selected bacteriophage is capable of infecting a host bacterial strain but is also capable of infecting a non-target host bacterial strain. A host bacterial strain is any bacterial strain that a selected phage is capable of infecting. A non-target host bacterial strain is any bacterial strain that a selected phage is capable of infecting that is disadvantageous for a desired use. In some embodiments, the selected phage is mutated to be incapable of infecting a non-target host bacterial strain.

The genus *Listeria* contains seven species (*monocytogenes, ivanovii, seeligeri, innocua, welshimeri, martii*, and *grayi*). Only two species are known to be pathogenic: *L. monocytogenes* and *L. ivanovii* (previously *L. monocytogenes* serotype 5). However, *L. ivanovii* primarily infects animals and rarely causes disease in humans. Serotyping differentiates isolates of *Listeria* below the species level. *L. monocytogenes* strains are serotyped according to variation in the somatic (O) and flagellar (H) antigens. The surface of bacteria are covered with lipopolysaccharide (LPS), and the outermost portion of the LPS is known as the O antigen. Somatic antigens are found in both gram-positive and gram-negative bacteria. The flagellum is a tail-like structure that aids in bacterium locomotion. The slender thread-like portion of the flagellum is referred to as the H antigen.

*L. monocytogenes* has a high genetic diversity and clonal population structure. Twelve serotypes of *L. monocytogenes* (1/2a, 1/2b, 1/2c, 3a, 3b, 3c, 4a, 4b, 4c, 4d, 4e, and 7) are recognized. Two major phylogenetic divisions within *L. monocytogenes* have been described. The first division consists of serotypes 1/2b, 3b, 4b, 4d, and 4e, and the second division consists of serotypes 1/2a, 1/2c, 3a, and 3c. Additionally, the less common serotypes 4a and 4c have also been described and make up a third division. Three serotypes (1/2a, 1/2b, and 4b) are responsible for causing the majority of clinical cases. Over 50% of *L. monocytogenes* isolated from food and the environment are serotype 1/2 (especially 1/2a and 1/2b). However, serotype 4b strains are the most prevalent cause of foodborne outbreaks of human listeriosis.

Some bacteriophages have a narrow host range, capable of infecting some serotypes of *L. monocytogenes* but not others. For example, some bacteriophages are specific for *Listeria monocytogenes* 19115 (serotype 4b), but are unable to detect other serotypes of *Listeria monocytogenes*, e.g., *Listeria monocytogenes* 51782 (serotype 3a). In some embodiments, the selected bacteriophage is specific for one serotype of *Listeria monocytogenes*, but is not capable of infecting another serotype of *Listeria monocytogenes*. In some instances the selected bacteriophage is specific for *Listeria monocytogenes* 19115 (serotype 4b) but is unable to infect *Listeria monocytogenes* 51782 (serotype 3a).

Some bacteriophages are known to have a broad host range, capable of infecting species of bacteria across multiple genera. For example, bacteriophage Mu is able to infect species of *Escherichia coli, Citrobacter freundii, Shigella sonnei*, and *Enterobacter*. Similarly, some bacteriophages are known to have a broad host range within a particular genera of bacteria. For example, multiple *Listeria*-specific bacteriophages, including A511 and P100, are capable of infecting several serotypes of *Listeria monocytogenes*, as well as other *Listeria* spp.

For certain applications, it may be advantageous to use a *Listeria*-specific bacteriophage having a broad host-range. For other applications, it may be advantageous to use a *Listeria*-specific phage capable of infecting multiple species of *Listeria*. Thus, is some embodiments, bacteriophages are mutated to be capable of infecting at least 2, 3, 4, 5, 6, and 7 species of *Listeria*. In other embodiments, bacteriophages are mutated to be capable of infecting at least 2, 3, 4, 5, 6, 7, 8, 9, 10, 11, or 12 serotypes of *L. monocytogenes*.

In some embodiments, the method comprises preparing a series of first co-culture mixtures of varying ratios comprising a host bacterial strain and a target-host bacterial strain. In further embodiments, a host bacterial strain and a target-host bacterial strain are cultured separately to obtain stock cultures of each. In certain embodiments, the host bacterial strain is for *Listeria monocytogenes* 19115 (serotype 4b). In further embodiments, the target bacterial strain is *Listeria monocytogenes* 51782 (serotype 3a). In other embodiments, the target bacterial strain is *Listeria monocytogenes* serotype 1/2a. In some embodiments, the target bacterial strain is *Listeria monocytogenes* serotype 1/2b. In still other embodiments, the target bacterial strain comprises one or more of the following *Listeria monocytogenes* serotypes: 1/2a, 1/2b, 1/2c, 3a, 3b, 3c, 4a, 4b, 4c, 4d, 4e, and 7.

After separately cultivating volumes of the host and target-host bacterial strains that have never been in the presence of the selected phage of interest, the bacterial cultures are combined in various ratios to one another to create a series of co-cultures. In one instance, the series of the plurality of first co-cultures comprises a ratio of 1:0, 9:1, 1:1, 1:9, and 0:1 of the host bacterial strain:the target-host bacterial strain. In other instances, the plurality of first co-cultures comprises any suitable ration between 1:0 and 0:1.

In further embodiments, the method comprises adding a phage strain to each of the first co-culture mixtures. The ratio of co-culture to phage may vary depending on the phage/host minimum Multiplicity of Infection (MOI) to cause productive culture infection. In some instances, the MOI is at least 0.1, 0.5, 1.0, 1.5, 2.0, 2.5, 3.0, 3.5, 4.0, 4.5, or 5.0. In certain embodiments the MOI is 1.0. In some embodiments, the phage strain is specific for *Listeria* spp. In other embodiments, the phage strain is specific for *Listeria monocytogenes*. In still other embodiments, the phage is specific for one serotype of *Listeria monocytogenes*. For example, the selected phage may be specific for *Listeria monocytogenes* 19115 (serotype 4b). In certain instances, the phage is selected from A511, P100, LMTA-94, LMA4, LMA8, P70, LP-ES1, LP-ES3A.

In certain instances, the method comprises incubating the first co-culture mixtures and the phage strain under bacterial culture conditions. A suitable growth medium for the host and/or target-host organisms is made with 1.2-1.5% agar, poured into sterile petri dishes, and allowed to solidify to create the "base layer". 300 μL of bacterial culture at mid-log is mixed with 100 μL of phage and incubated at RT while rocking for 15-20 minutes. The infected culture is then mixed with 4 mL of molten (50-55° C.) medium suitable for the bacteria being grown, made with 0.7-1.0% agar and poured over the top of the base agar layer in the petri dish. The "top layer" is allowed to cool to RT and solidify and is then incubated for 12-15 hours under optimal growth conditions for the bacterial strain being cultured.

In some embodiments, the method comprises collecting a phage lysate from each of the plurality of first-co-cultures. In certain embodiments, following incubation, the phage lysate is separated from each of the first co-culture mixture ratios. In some embodiments, each co-culture mixture is centrifuged and the supernatant is filtered to obtain a phage lysate. For example, each co-culture may be centrifuged at 3220×g at RT for 20 minutes. In some embodiments the filter is less than 0.75, 0.65, 0.55, 0.45, 0.35, 0.25, or 0.15 μm. In certain embodiments, the filter is 0.45 μm. In some instances, the phage lysates from each of the plurality of first co-cultures are pooled to obtain a single volume of phage lysates.

In some embodiments, the method comprises assaying phage lysates to determine if the bacteria host-range has expanded. In some instances the pooled phage lysates are plated for single plaques on the identified host strain and on the selected target-host strain. For example, a double-overlay assay may be used to check for bacteriophage specificity against the host and target-host organisms. Naïve mid-log cultures of the host and target-host bacteria are propagated and used in double-overlay assays. If plaque forming units (PFU) are formed than infective activity against the organism used in the assay is detected. This step ensures that infective activity against the original host is not lost and exposes mutant phage that have undergone the desired host-expansion event.

In some embodiments, the pooled phage lysate is then passaged into the plurality of first co-cultures, isolated, and assayed again, as described in detail herein. Passaging is repeated until mutant phage that infects the target-host bacterial strain is detected. In some embodiments, phage are passage at least 2, 3, 4, 5, 6, 7, 8, 9, or 10 times.

In some embodiments, the method comprises isolating a mutant phage with expanded host-range. Following confirmation of activity against both the host and target-host organisms, the method comprises isolating the mutant phage. In some embodiments, the isolated mutant phage population is then expanded to produce a stock of mutant phage.

The disclosed methods present procedures that cause phage to infect a predetermined bacterial host that it otherwise would not infect.

Thus, the methods of the present invention utilize the high specificity of binding agents, associated with infectious agents, that recognize and bind to a particular microorganism of interest.

In other applications, it may be advantageous to use a bacteriophage having a more narrow host-range. For example, it may be advantageous to use a *Listeria*-specific phage capable of infecting only the clinically relevant serotypes (1/2a, 1/2b, and 4b) and unable to infect non-pathogenic *Listeria* serotypes. Thus, in some embodiments, bacteriophages are mutated to be capable of infecting pathogenic serotypes of *L. monocytogenes* and unable to infect non-pathogenic serotypes of *L. monocytogenes.*

In some embodiments, the host range of a bacteriophage can be reduced or altered by modifying proteins responsible for host specificity. Bacterial host specificity can be dictated by cell wall-binding domains (CBDs) or other proteins present in bacteriophages. CBDs are important for specific cell-wall recognition and can be present in from an endolysin, or a spanin, or a tail fiber, or a tail spike protein. For example, tail spike proteins bind to the cell surface of bacterial hosts and mediate bacterial host recognition. Thus, mutation of tail spike proteins can be used to change the ability of a mutated bacteriophage to recognize a particular bacterial strain.

Thus, in some embodiments, genes encoding tail fiber or tail spike proteins may be mutated to alter or reduce the specificity of a particular bacteriophage. For example a bacteriophage may have two tail spike protein—one providing specificity for a first *L. monocytogenes* serotype (e.g., 4b) and a second providing specificity for a second *L. monocytogenes* serotype (e.g., 7). Thus, in some embodiments, one tail spike protein may be mutated in order to alter the specificity of the bacteriophage. Any molecular method generally known in the art for mutating bacteriophages may be used to alter tail fiber/tail spike proteins such that the specificity of a bacteriophage is narrowed. For example, a bacteriophage may be subjected to a random mutagenesis protocol.

In some instances, the bacteriophage genome may be partitioned into overlapping DNA fragments. The fragment encoding the tail spike protein of interest (i.e., the tail spike protein specific for the serotype that is not of interest) may be amplified using error-prone PCR to introduce targeted mutagenesis within the gene. The fragments of genomic DNAs may then be reassembled to produce a library of phage genomes. The pooled phage genome may then be transfected into *Listeria* thereby producing mutated progeny phage. Progeny phage may then be assayed for plaque formation on *Listeria* stains of interest. Viable phage mutants with the desired specificity may then be isolated.

Thus in some embodiments, the present disclosure is directed to a method of producing a mutant bacteriophage with a reduced host-range. In some embodiments, the method comprises (i) mutating a gene encoding a tail spike protein of a bacteriophage (ii) producing progeny phage lysates from the mutated bacteriophage; (iii) assaying phage lysates to determine if the bacteria host-range has reduced; and (iv) isolating a mutant phage with reduced host-range.

Indicator Mutant Bacteriophage

As described in more detail herein, the compositions and methods of the present disclosure may comprise infectious agents for use in detection of pathogenic microorganisms In certain embodiments, the present disclosure comprises a recombinant indicator mutant bacteriophage, wherein the bacteriophage genome is genetically modified to include an indicator or reporter gene. In some embodiments, the present disclosure may include a composition comprising a recombinant mutant bacteriophage having an indicator gene incorporated into the genome of the previously mutated bacteriophage. In some embodiments, the mutant bacteriophage is produced according to the methods described in detail herein. In some embodiments, the mutant bacteriophage has an expanded and/or reduced host-range.

A recombinant indicator mutant bacteriophage can include a reporter or indicator gene. In certain embodiments of the infectious agent, the indicator gene does not encode a fusion protein. For example, in certain embodiments, expression of the indicator gene during bacteriophage replication following infection of a host bacterium results in a soluble indicator protein product. In certain embodiments, the indicator gene may be inserted into a late gene region of the mutant bacteriophage. Late genes are generally expressed at higher levels than other phage genes, as they code for structural proteins. The late gene region may be a class III gene region and may include a gene for a major capsid protein.

Some embodiments include designing (and optionally preparing) a sequence for homologous recombination downstream of the major capsid protein gene. Other embodiments include designing (and optionally preparing) a sequence for homologous recombination upstream of the major capsid protein gene. In some embodiments, the sequence comprises a codon-optimized reporter gene preceded by an untranslated region. The untranslated region may include a phage late gene promoter and ribosomal entry site.

In some embodiments, the selected wild-type bacteriophage is from the Caudovirales order of phages. Caudovirales are an order of tailed bacteriophages with double-stranded DNA (dsDNA) genomes. Each virion of the Caudovirales order has an icosahedral head that contains the viral genome and a flexible tail. The Caudovirales order comprises five bacteriophage families: Myoviridae (long contractile tails), Siphoviridae (long non-contractile tails), Podoviridae (short non-contractile tails), Ackermannviridae, and Herelleviridae. The term myovirus can be used to describe any bacteriophage with an icosahedral head and a long contractile tail, which encompasses bacteriophages within both the Myoviridae and Herelleviridae families. In some embodiments, the selected wild-type bacteriophage is a member of the Myoviridae family such as, *Listeria* phage B054, *Listeria* phage LipZ5, *Listeria* phage PSU-VKH-LP041, and *Listeria* phage WIL-2. In other embodiments, the selected wild-type bacteriophage is a member of the family Herelleviridae. The genus *Pecentumvirus*, under the family Herelleviridae includes bacteriophages such as *Listeria* phage LMSP-25, *Listeria* phage LMTA-148, *Listeria* phage LMTA-34, *Listeria* phage LP-048, *Listeria* phage LP-064, *Listeria* phage LP-083-2, *Listeria* phage LP-125, *Listeria* virus P100, *Listeria* phage List-36, *Listeria* phage WIL-1, *Listeria* phage vB_LmoM_AG20, and *Listeria* virus A511. LMA4 and LMA8 are also likely in the genus *Pecentumvirus*, under the family Herelleviridae. In other embodiments, the selected wild-type bacteriophage is LMA4 or LMA8. In certain instances the selected wild-type bacteriophage is LP-ES3A, which is derived from A511 but has been adapted to be capable of infecting serotype 3A of *Listeria monocytogenes*. In still other embodiments, the selected wild-type bacteriophage is a member of the family Ackermannviridae. In still other embodiments, the selected wild-type bacteriophage is a member of the family Siphoviridae, which includes *Listeria* phages A006, A118, A500, B025, LP-026, LP-030-2, LP-030-3, LP-037, LP-101, LP-110, LP-114, P35, P40, P70, PSA, vB_LmoS_188, and vB_Lmos_293. In other embodiments, the selected wild-type bacteriophage is LP-ES1. LP-ES1 is also likely in the genus *Homburgvirus*, under the family Siphoviridae.

In some embodiments, an indicator bacteriophage is derived from *Listeria*-specific phage. An indicator bacteriophage may be constructed from a *Pecentumvirus*, Tequatravirus, ViI, Kuttervirus, *Homburgvirus*, A511, P100, P70, LMTA-94, LMA4, LMA8, P70, LP-ES1, LP-ES3A or another bacteriophage having a genome with at least 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% homology to *Listeria* phage LMTA-94, P70, T7, T7-like, T4, T4-like, *Listeria* spp.-specific bacteriophage, ViI, or ViI-like (Kuttervirus, per GenBank/NCBI) bacteriophages. In other embodiments, the selected wild-type bacteriophage is A511, P100, P70, LP-ES1, LP-ES3A, LMA4 or LMA8. In some embodiments, the indicator phage is derived from a bacteriophage that is highly specific for a particular pathogenic microorganism. The genetic modifications may avoid deletions of wild-type genes and thus the modified phage may remain more similar to the wild-type infectious agent than many commercially available phage. Environmentally derived bacteriophage may be more specific for bacteria that are found in the environment and as such, genetically distinct from phage available commercially.

In another aspect of the invention, a cocktail composition comprises at least one type of recombinant bacteriophage. In some embodiments, the cocktail composition comprises at least one type of recombinant bacteriophage constructed from LMA4, LMA8, A511, P70, LP-ES1, and LP-ES3A. In other embodiments, the cocktail composition comprises at least one type of recombinant bacteriophage constructed from LMA8, LP-ES1, and LP-ES3A.

Moreover, phage genes thought to be nonessential may have unrecognized function. For example, an apparently nonessential gene may have an important function in elevating burst size such as subtle cutting, fitting, or trimming functions in assembly. Therefore, deleting genes to insert an indicator may be detrimental. Most phages can package DNA that is a few percent larger than their natural genome. With this consideration, a smaller indicator gene may be a more appropriate choice for modifying a bacteriophage, especially one with a smaller genome. OpLuc and NANOLUC® proteins are only about 20 kDa (approximately 500-600 bp to encode), while FLuc is about 62 kDa (approximately 1,700 bp to encode). For comparison, the genome of T7 is around 40 kbp, while the T4 genome is about 170 kbp, and the genome of *Listeria*-specific bacteriophage is about 157 kbp. Moreover, the reporter gene should not be expressed endogenously by the bacteria (i.e., is not part of the bacterial genome), should generate a high signal to background ratio, and should be readily detectable in a timely manner. Promega's NANOLUC® is a modified Oplophorus gracilirostris (deep sea shrimp) luciferase. In some embodiments, NANOLUC® combined with Promega's NANO-GLO®, an imidazopyrazinone substrate (furimazine), can provide a robust signal with low background.

In some indicator mutant phage embodiments, the indicator gene can be inserted into an untranslated region to avoid disruption of functional genes, leaving wild-type phage genes intact, which may lead to greater fitness when infecting non-laboratory strains of bacteria. Additionally, including stop codons in all three reading frames may help to increase expression by reducing read-through, also known as leaky expression. This strategy may also eliminate the possibility of a fusion protein being made at low levels, which would manifest as background signal (e.g., luciferase) that cannot be separated from the phage.

An indicator gene may express a variety of biomolecules. The indicator gene is a gene that expresses a detectable product or an enzyme that produces a detectable product. For example, in one embodiment the indicator gene encodes a luciferase enzyme. Various types of luciferase may be used In alternate embodiments, and as described in more detail herein, the luciferase is one of Oplophorus luciferase, Firefly luciferase, Lucia luciferase, Renilla luciferase, or an engineered luciferase. In some embodiments, the luciferase gene is derived from Oplophorus. In some embodiments, the indicator gene is a genetically modified luciferase gene, such as NANOLUC®.

Thus, in some embodiments, the present invention comprises a genetically modified bacteriophage comprising a non-bacteriophage indicator gene in the late (class III) gene region. In some embodiments, the non-native indicator gene is under the control of a late promoter. Using a viral late gene promoter insures the reporter gene (e.g., luciferase) is not only expressed at high levels, like viral capsid proteins, but also does not shut down like endogenous bacterial genes or even early viral genes.

In some embodiments, the late promoter is a *Pecentumvirus*, Tequatravirus, *Homburgvirus*, or Kuttervirus promoter, or another phage promoter similar to that found in the selected wild-type phage, i.e., without genetic modification. The late gene region may be a class III gene region, and the bacteriophage may be derived from *Listeria* phage LMTA-94, P70, A511, LP-ES1, LP-ES3A, LMA4, LMA8, *Pecentumvirus*, Tequatravirus, *Homburgvirus*, Kuttervirus, T7, T4, T4-like, ViI, *Listeria* spp.-specific bacteriophage, or another wild-type bacteriophage having a genome with at least 70, 75, 80, 85, 90 or 95% homology to LMTA-94, LMA4, LMA8, *Pecentumvirus*, Tequatravirus, *Homburgvirus*, Kuttervirus, T7, T4, ViI, or *Listeria*-specific bacteriophage. The *Pecentumvirus* late gene promoter is distinct from the T4 or Tequatravirus promoter, as it consists of not only the −10 region, but also a −35 region. This −35 region differs from the standard −35 region found in most bacterial promoters.

Genetic modifications to infectious agents may include insertions, deletions, or substitutions of a small fragment of nucleic acid, a substantial part of a gene, or an entire gene. In some embodiments, inserted or substituted nucleic acids comprise non-native sequences. A non-native indicator gene may be inserted into a bacteriophage genome such that it is under the control of a bacteriophage promoter. Thus, in some embodiments, the non-native indicator gene is not part of a fusion protein. That is, in some embodiments, a genetic modification may be configured such that the indicator protein product does not comprise polypeptides of the wild-type bacteriophage. In some embodiments, the indicator protein product is soluble. In some embodiments, the invention comprises a method for detecting a bacterium of interest comprising the step of incubating a test sample with such a recombinant bacteriophage.

In some embodiments, expression of the indicator gene in progeny bacteriophage following infection of host bacteria results in a free, soluble protein product. In some embodiments, the non-native indicator gene is not contiguous with a gene encoding a structural phage protein and therefore does not yield a fusion protein. Unlike systems that employ a fusion of a detection moiety to the capsid protein (i.e., a fusion protein), some embodiments of the present invention express a soluble indicator or reporter (e.g., soluble luciferase). In some embodiments, the indicator or reporter is ideally free of the bacteriophage structure. That is, the indicator or reporter is not attached to the phage structure. As such, the gene for the indicator or reporter is not fused with other genes in the recombinant phage genome This may greatly increase the sensitivity of the assay (down to a single bacterium), and simplify the assay, allowing the assay to be completed in two hours or less for some embodiments, as opposed to several hours due to additional purification steps required with constructs that produce detectable fusion proteins. Further, fusion proteins may be less active than soluble proteins due, e.g., to protein folding constraints that may alter the conformation of the enzyme active site or access to the substrate. If the concentration is 10 bacterial cells/mL of sample, for example, less than two hours may be sufficient for the assay.

Moreover, fusion proteins by definition limit the number of the moieties attached to subunits of a protein in the bacteriophage. For example, using a commercially available system designed to serve as a platform for a fusion protein would result in about 415 copies of the fusion moiety, corresponding to the about 415 copies of the gene 10B capsid protein in each T7 bacteriophage particle. Without this constraint, infected bacteria can be expected to express many more copies of the indicator protein product (e.g., luciferase) than can fit on the bacteriophage. Additionally, large fusion proteins, such as a capsid-luciferase fusion, may inhibit assembly of the bacteriophage particle, thus yielding fewer bacteriophage progeny. Thus a soluble, non-fusion indicator gene product may be preferable.

In some embodiments, the indicator phage encodes a reporter, such as a detectable enzyme. The indicator gene product may generate light and/or may be detectable by a color change. Various appropriate enzymes are commercially available, such as alkaline phosphatase (AP), horseradish peroxidase (HRP), or luciferase (Luc). In some embodiments, these enzymes may serve as the indicator protein product. In some embodiments, Firefly luciferase is the indicator protein product. In some embodiments, Oplophorus luciferase is the indicator protein product. In some embodiments, NANOLUC® is the indicator moiety. Other engineered luciferases or other enzymes that generate detectable signals may also be appropriate indicator protein products.

In some embodiments, the use of a soluble indicator protein eliminates the need to remove contaminating parental phage from the lysate of the infected sample cells. With a fusion protein system, any bacteriophage used to infect sample cells would have the detection moiety attached, and would be indistinguishable from the daughter bacteriophage also containing the detection moiety. As detection of sample bacteria relies on the detection of a newly created (de novo synthesized) detection moiety, using fusion constructs requires additional steps to separate old (parental) moieties from newly created (daughter bacteriophage) moieties. This may be accomplished by washing the infected cells multiple times, prior to the completion of the bacteriophage life cycle, inactivating excess parental phage after infection by physical or chemical means, and/or chemically modifying the parental bacteriophage with a binding moiety (such as biotin), which can then be bound and separated (such as by streptavidin-coated sepharose beads). However, even with all these attempts at removal, parental phage can remain when a high concentration of parental phage is used to assure infection of a low number of sample cells, creating background signal that may obscure detection of signal from infected cell progeny phage.

By contrast, with the soluble indicator protein product expressed in some embodiments of the present invention, purification of the parental phage from the final lysate is unnecessary, as the parental phage do not have any indicator protein attached. Thus any indicator protein present after infection must have been created de novo, indicating the presence of an infected bacterium or bacteria. To take advantage of this benefit, the production and preparation of parental phage may include purification of the phage from any free indicator protein produced during the production of parental bacteriophage in bacterial culture. Standard bacteriophage purification techniques may be employed to purify some embodiments of phage according to the present invention, such as sucrose density gradient centrifugation, cesium chloride isopycnic density gradient centrifugation, HPLC, size exclusion chromatography, and dialysis or derived technologies (such as Amicon brand concentrators—Millipore, Inc.). Cesium chloride isopycnic ultracentrifugation can be employed as part of the preparation of recombinant phage of the invention, to separate parental phage particles from contaminating luciferase protein produced upon propagation of the phage in the bacterial host. In this way, the parental recombinant bacteriophage of the invention is substantially free of any luciferase generated during production in the bacteria. Removal of residual luciferase present in the phage stock can substantially reduce background signal observed when the recombinant bacteriophage are incubated with a test sample.

In some embodiments of modified bacteriophage, the late promoter (class III promoter, e.g., from *Pecentumvirus, Homburgvirus*, T7, T4, ViI, or LMA4/8) has high affinity for RNA polymerase of the same bacteriophage that transcribes genes for structural proteins assembled into the bacteriophage particle. These proteins are the most abundant proteins made by the phage, as each bacteriophage particle comprises dozens or hundreds of copies of these molecules. The use of a viral late promoter can ensure optimally high level of expression of the luciferase indicator protein. The use of a late viral promoter derived from, specific to, or active under the original wild-type bacteriophage the indicator phage is derived from (e.g., a *Pecentumvirus, Homburgvirus*, T4, T7, ViI, or LMA4/8 late promoter with a *Pecentumvirus*, T4, T7-, ViI-, or LMA-based system) can further ensure optimal expression of the indicator protein. The use of a standard bacterial (non-viral/non-bacteriophage) promoter may in some cases be detrimental to expression, as these promoters are often down-regulated during bacteriophage infection (in order for the bacteriophage to prioritize the bacterial resources for phage protein production). Thus, in some embodiments, the phage is preferably engineered to encode and express at high level a soluble (free) indicator protein, using a placement in the genome that does not limit expression to the number of subunits of a phage structural component.

Compositions of the present disclosure may comprise one or more wild-type or genetically modified infectious agents (e.g., bacteriophages) and one or more indicator genes. In some embodiments, compositions can include cocktails of different indicator phages that may encode and express the same or different indicator proteins. In some embodiments, the cocktail of bacteriophage comprises at least two different types of recombinant bacteriophages.

Methods of Using Mutant Bacteriophage for Detecting *Listeria* Spp

As noted herein, in certain embodiments, the present disclosure is directed to methods of using infectious particles for detecting microorganisms.

In another aspect, the present disclosure is directed to a method for detecting a bacterium of interest in a sample comprising the steps of: incubating the sample with bacteriophage that infects a host and target host bacterium of interest, wherein the bacteriophage comprises an indicator gene such that expression of the indicator gene during bacteriophage replication following infection of the bacterium of interest results in production of a soluble indicator protein product; and detecting the indicator protein product, wherein positive detection of the indicator protein product indicates that the bacterium of interest is present in the sample.

In some embodiments, a selected bacteriophage is mutated, as described in detailed herein, to expand and/or reduce host-range. In some embodiments, the selected bacteriophage may be specific to one serotype of *Listeria monocytogenes*. For example, some bacteriophage are specific for *Listeria monocytogenes* 19115 (serotype 4b), but are unable to detect other serotypes of *Listeria monocytogenes*, e.g., *Listeria monocytogenes* 51782 (serotype 3a). In some embodiments, the selected bacteriophage is specific for one serotype of *Listeria monocytogenes*, but is not capable of infecting another serotype of *Listeria monocytogenes*. In some instances the selected bacteriophage is specific for *Listeria monocytogenes* 19115 (serotype 4b) but is unable to infect *Listeria monocytogenes* 51782 (serotype 3a).

In some embodiments, the mutated bacteriophage infects a host and target-host bacterium of interest. In certain embodiments, the host bacterial strain is for *Listeria monocytogenes* 19115 (serotype 4b). In further embodiments, the target bacterial strain is *Listeria monocytogenes* 51782 (serotype 3a).

In some embodiments, the mutant bacteriophage may be engineered to express a soluble luciferase during replication of the phage. Expression of luciferase is driven by a viral capsid promoter (e.g., the bacteriophage T7 or T4 late promoter), yielding high expression. Parental phage are prepared such that they are free of luciferase, so the luciferase detected in the assay must come from replication of progeny phage during infection of the bacterial cells. Thus, there is generally no need to separate out the parental phage from the progeny phage.

In some embodiments, enrichment of bacteria in the sample is not needed prior to testing. In some embodiments, the sample may be enriched prior to testing by incubation in conditions that encourage growth. In such embodiments, the enrichment period can be 1, 2, 3, 4, 5, 6, 7, 8, 9, 10, 11, 12, 13, 14, 15, 16, 17, 18, 19, 20, 21, 22, 23, or 24 hours or longer, depending on the sample type and size.

In an embodiment, the invention may comprise a method for detecting a bacterium of interest in a sample comprising the steps of: incubating the sample with a recombinant bacteriophage that infects the bacterium of interest, wherein the recombinant bacteriophage comprises an indicator gene inserted into a late gene region of the bacteriophage such that expression of the indicator gene during bacteriophage replication following infection of host bacteria results in production of a soluble indicator protein product; and detecting the indicator protein product, wherein positive detection of the indicator protein product indicates that the bacterium of interest is present in the sample. In some embodiments, the amount of indicator protein detected corresponds to the amount of the bacterium of interest present in the sample.

As described in more detail herein, the methods may utilize a range of concentrations of parental indicator bacteriophage to infect bacteria present in the sample. In some embodiments the indicator bacteriophage are added to the sample at a concentration sufficient to rapidly find, bind, and infect target bacteria that are present in very low numbers in the sample, such as a single cell. In some embodiments, the phage concentration can be sufficient to find, bind, and infect the target bacteria in less than one hour. In other embodiments, these events can occur in less than two hours, or less than three hours, or less than four hours, following addition of indicator phage to the sample. For example, in certain embodiments, the bacteriophage concentration for the incubating step is greater than $1\times10^5$ PFU/mL, greater than $1\times10^6$ PFU/mL, or greater than $1\times10^7$ PFU/mL.

In certain embodiments, the recombinant infectious agent may be purified so as to be free of any residual indicator protein that may be generated upon production of the infectious agent stock. Thus, in certain embodiments, the recombinant bacteriophage may be purified using cesium chloride isopycnic density gradient centrifugation prior to incubation with the sample. When the infectious agent is a bacteriophage, this purification may have the added benefit of removing bacteriophage that do not have DNA (i.e., empty phage or "ghosts").

In some embodiments of the methods of the invention, the microorganism may be detected without any isolation or purification of the microorganisms from a sample. For example, in certain embodiments, a sample containing one or a few microorganisms of interest may be applied directly to an assay container such as a spin column, a microtiter well, or a filter and the assay is conducted in that assay container. Various embodiments of such assays are disclosed herein.

Aliquots of a test sample may be distributed directly into wells of a multi-well plate, indicator phage may be added, and after a period of time sufficient for infection, a lysis buffer may be added as well as a substrate for the indicator protein (e.g., luciferase substrate for a luciferase indicator) and assayed for detection of the indicator signal. Some embodiments of the method can be performed on filter plates. Some embodiments of the method can be performed with or without concentration of the sample before infection with indicator phage.

For example, in many embodiments, multi-well plates are used to conduct the assays. The choice of plates (or any other container in which detecting may be performed) may affect the detecting step. For example, some plates may include a colored or white background, which may affect the detection of light emissions. Generally speaking, white plates have higher sensitivity but also yield a higher background signal. Other colors of plates may generate lower background signal but also have a slightly lower sensitivity. Additionally, one reason for background signal is the leakage of light from one well to another, adjacent well. There are some plates that have white wells but the rest of the plate is black. This allows for a high signal inside the well but prevents well-to-well light leakage and thus may decrease background. Thus the choice of plate or other assay vessel may influence the sensitivity and background signal for the assay.

Methods of the invention may comprise various other steps to increase sensitivity. For example, as discussed in more detail herein, the method may comprise a step for washing the captured and infected bacterium, after adding the bacteriophage but before incubating, to remove excess parental bacteriophage and/or luciferase or other reporter protein contaminating the bacteriophage preparation.

In some embodiments, detection of the microorganism of interest may be completed without the need for culturing the sample as a way to increase the population of the microorganisms. For example, in certain embodiments the total time required for detection is less than 28.0 hours, 27.0 hours, 26.0 hours, 25.0 hours, 24.0 hours, 23.0 hours, 22.0 hours, 21.0 hours, 20.0 hours, 19.0 hours, 18.0 hours, 17.0 hours, 16.0 hours, 15.0 hours, 14.0 hours, 13.0 hours, 12.0 hours, 11.0 hours, 10.0 hours, 9.0 hours, 8.0 hours, 7.0 hours, 6.0 hours, 5.0 hours, 4.0 hours, 3.0 hours, 2.5 hours, 2.0 hours, 1.5 hours, 1.0 hour, 45 minutes, or less than 30 minutes. Minimizing time to result is critical in food and environmental testing for pathogens.

In contrast to assays known in the art, the method of the invention can detect individual microorganisms. Thus, in certain embodiments, the method may detect ≤10 cells of the microorganism (i.e., 1, 2, 3, 4, 5, 6, 7, 8, 9 microorganisms) present in a sample. For example, in certain embodiments, the recombinant bacteriophage is highly specific for *Listeria* spp. In an embodiment, the recombinant bacteriophage can distinguish *Listeria* spp. in the presence of other types of bacteria. In certain embodiments, the recombinant bacteriophage can be used to detect a single bacterium of the specific type in the sample. In certain embodiments, the recombinant bacteriophage detects as few as 2, 3, 4, 5, 6, 7, 8, 9, 10, 15, 20, 30, 40, 50, 60, 70, 80, 90, or 100 of the specific bacteria in the sample.

Thus, aspects of the present invention provide methods for detection of microorganisms in a test sample via an indicator protein. In some embodiments, where the microorganism of interest is a bacterium, the indicator protein may be associated with an infectious agent such as an indicator bacteriophage. The indicator protein may react with a substrate to emit a detectable signal or may emit an intrinsic signal (e.g., fluorescent protein). In some embodiments, the detection sensitivity can reveal the presence of as few as 50, 20, 10, 9, 8, 7, 6, 5, 4, 3, or 2 cells of the microorganism of interest in a test sample. In some embodiments, even a single cell of the microorganism of interest may yield a detectable signal. In some embodiments, the bacteriophage is a P100virus, T4-like or ViI-like bacteriophage. In some embodiments, the recombinant bacteriophage is derived from *Listeria*-specific bacteriophage. In certain embodiments, a recombinant *Listeria*-specific bacteriophage is highly specific for *Listeria* spp.

In some embodiments, the indicator protein encoded by the infectious agent may be detectable during or after replication of the infectious agent. Many different types of detectable biomolecules suitable for use as indicator moieties are known in the art, and many are commercially available. In some embodiments the indicator phage comprises an enzyme, which serves as the indicator protein. In some embodiments, the genome of the indicator phage is modified to encode a soluble protein. In some embodiments, the indicator phage encodes a detectable enzyme. The indicator may emit light and/or may be detectable by a color change in an added substrate. Various appropriate enzymes are commercially available, such as alkaline phosphatase (AP), horseradish peroxidase (HRP), or luciferase (Luc). In some embodiments, these enzymes may serve as the indicator protein. In some embodiments, Firefly luciferase is the indicator protein. In some embodiments, Oplophorus luciferase is the indicator protein. In some embodiments, NANOLUC® is the indicator protein. Other engineered luciferases or other enzymes that generate detectable signals may also be appropriate indicator proteins.

Thus, in some embodiments, the recombinant bacteriophage of the methods, systems or kits is prepared from wild-type *Listeria*-specific bacteriophage. In some embodiments, the indicator gene encodes a protein that emits an intrinsic signal, such as a fluorescent protein (e.g., green fluorescent protein or others). The indicator may emit light and/or may be detectable by a color change. In some embodiments, the indicator gene encodes an enzyme (e.g., luciferase) that interacts with a substrate to generate signal. In some embodiments, the indicator gene is a luciferase gene. In some embodiments, the luciferase gene is one of Oplophorus luciferase, Firefly luciferase, Renilla luciferase, External Gaussia luciferase, Lucia luciferase, or an engineered luciferase such as NANOLUC®, Rluc8.6-535, or Orange Nano-lantern.

Detecting the indicator may include detecting emissions of light. In some embodiments, a luminometer may be used to detect the reaction of indicator (e.g., luciferase) with a substrate. The detection of RLU can be achieved with a luminometer, or other machines or devices may also be used. For example, a spectrophotometer, CCD camera, or CMOS camera may detect color changes and other light emissions. Absolute RLU are important for detection, but the signal to background ratio also needs to be high (e.g., >2.0, >2.5, or >3.0) in order for single cells or low numbers of cells to be detected reliably.

In some embodiments, the indicator phage is genetically engineered to contain the gene for an enzyme, such as a luciferase, which is only produced upon infection of bacteria that the phage specifically recognizes and infects. In some embodiments, the indicator protein is expressed late in the viral life cycle. In some embodiments, as described herein, the indicator is a soluble protein (e.g., soluble luciferase) and is not fused with a phage structural protein that limits its copy number.

Thus in some embodiments utilizing indicator phage, the invention comprises a method for detecting a microorganism of interest comprising the steps of capturing at least one sample bacterium; incubating the at least one bacterium with a plurality of indicator phage; allowing time for infection and replication to generate progeny phage and express soluble indicator protein; and detecting the progeny phage, or preferably the indicator, wherein detection of the indicator demonstrates that the bacterium is present in the sample.

For example, in some embodiments the test sample bacterium may be captured by binding to the surface of a plate, or by filtering the sample through a bacteriological filter (e.g., 0.45 μm pore size spin filter or plate filter). In an embodiment, the infectious agent (e.g., indicator phage) is added in a minimal volume to the captured sample directly on the filter. In an embodiment, the microorganism captured on the filter or plate surface is subsequently washed one or more times to remove excess unbound infectious agent. In an embodiment, a medium (e.g., Luria-Bertani Broth, also called LB herein, Buffered Peptone Water, also called BPW herein, or Tryptic Soy Broth or Tryptone Soy Broth, also called TSB herein) may be added for further incubation time, to allow replication of bacterial cells and phage and high-level expression of the gene encoding the indicator protein. However, a surprising aspect of some embodiments of testing assays is that the incubation step with indicator phage only needs to be long enough for a single phage life cycle. The amplification power of using bacteriophage was previously thought to require more time, such that the phage would replicate for several cycles. A single replication cycle of indicator phage can be sufficient to facilitate sensitive and rapid detection according to some embodiments of the present invention.

In some embodiments, aliquots of a test sample comprising bacteria may be applied to a spin column and after infection with a recombinant bacteriophage and an optional washing to remove any excess bacteriophage, the amount of soluble indicator detected will be proportional to the amount of bacteriophage that are produced by infected bacteria.

Soluble indicator protein (e.g., luciferase) released into the surrounding liquid upon lysis of the bacteria may then be measured and quantified. In an embodiment, the solution is spun through the filter, and the filtrate collected for assay in a new receptacle (e.g., in a luminometer) following addition of a substrate for the indicator enzyme (e.g., luciferase substrate). Alternatively, the indicator signal may be measured directly on the filter.

In various embodiments, the purified parental indicator phage does not comprise the detectable indicator itself, because the parental phage can be purified before it is used for incubation with a test sample. Expression of late (Class III) genes occurs late in the viral life cycle. In some embodiments of the present invention, parental phage may be purified to exclude any existing indicator protein (e.g., luciferase). In some embodiments, expression of the indicator gene during bacteriophage replication following infection of host bacteria results in a soluble indicator protein product. Thus, in many embodiments, it is not necessary to separate parental from progeny phage prior to the detecting step. In an embodiment, the microorganism is a bacterium and the indicator phage is a bacteriophage. In an embodiment, the indicator moiety is soluble luciferase, which is released upon lysis of the host microorganism.

Thus, in an alternate embodiment, the indicator substrate (e.g., luciferase substrate) may be incubated with the portion of the sample that remains on a filter or bound to a plate surface. Accordingly, in some embodiments the solid support is a 96-well filter plate (or regular 96-well plate), and the substrate reaction may be detected by placing the plate directly in the luminometer.

For example, in an embodiment, the invention may comprise a method for detecting *Listeria* spp. comprising the steps of: infecting cells captured on a 96-well filter plate with a plurality of parental indicator phage capable of expressing luciferase upon infection; washing excess phage away; adding LB broth and allowing time for phage to replicate and lyse the specific *Listeria* spp. target (e.g., 30-120 minutes); and detecting the indicator luciferase by adding luciferase substrate and measuring luciferase activity directly in the 96-well plate, wherein detection of luciferase activity indicates that the *Listeria* spp. is present in the sample.

In another embodiment, the invention may comprise a method for detecting *Listeria* spp. comprising the steps of: infecting cells in liquid solution or suspension in a 96-well plate with a plurality of parental indicator phage capable of expressing luciferase upon infection; allowing time for phage to replicate and lyse the specific *Listeria* spp. target (e.g., 30-120 minutes); and detecting the indicator luciferase by adding luciferase substrate and measuring luciferase activity directly in the 96-well plate, wherein detection of luciferase activity indicates that the *Listeria* spp. is present in the sample. In such an embodiment no capturing step is necessary. In some embodiments, the liquid solution or suspension may be a consumable test sample, such as a vegetable wash. In some embodiments, the liquid solution or suspension may be vegetable wash fortified with concentrated LB Broth, Tryptic/Tryptone Soy Broth, Peptone Water or Nutrient Broth. In some embodiments, the liquid solution or suspension may be bacteria diluted in LB Broth.

In some embodiments, lysis of the bacterium may occur before, during, or after the detection step. Experiments suggest that infected unlysed cells may be detectable upon addition of luciferase substrate in some embodiments. Presumably, luciferase may exit cells and/or luciferase substrate may enter cells without complete cell lysis. Thus, for embodiments utilizing the spin filter system, where only luciferase released into the lysate (and not luciferase still inside intact bacteria) is analyzed in the luminometer, lysis is required for detection. However, for embodiments utilizing filter plates or 96-well plates with sample in solution or suspension, where the original plate full of intact and lysed cells is directly assayed in the luminometer, lysis is not necessary for detection.

In some embodiments, the reaction of indicator protein product (e.g., luciferase) with substrate may continue for 30 minutes or more, and detection at various time points may be desirable for optimizing sensitivity. For example, in embodiments using 96-well filter plates as the solid support and luciferase as the indicator, luminometer readings may be taken initially and at 10- or 15-minute intervals until the reaction is completed.

Surprisingly, high concentrations of phage utilized for infecting test samples have successfully achieved detection of very low numbers of target microorganism in a very short timeframe. The incubation of phage with a test sample in some embodiments need only be long enough for a single phage life cycle. In some embodiments, the bacteriophage concentration for this incubating step is greater than $7\times10^6$, $8\times10^6$, $9\times10^6$, $1.0\times10^7$, $1.1\times10^7$, $1.2\times10^7$, $1.3\times10^7$, $1.4\times10^7$, $1.5\times10^7$, $1.6\times10^7$, $1.7\times10^7$, $1.8\times10^7$, $1.9\times10^7$, $2.0\times10^7$, $3.0\times10^7$, $4.0\times10^7$, $5.0\times10^7$, $6.0\times10^7$, $7.0\times10^7$, $8.0\times10^7$, $9.0\times10^7$, or $1.0\times10^8$ PFU/mL.

Success with such high concentrations of phage is surprising because the large numbers of phage were previously associated with "lysis from without," which killed target cells and thereby prevented generation of useful signal from earlier phage assays. It is possible that the clean-up of prepared phage stocks described herein helps to alleviate this problem (e.g., clean-up by cesium chloride isopycnic density gradient ultracentrifugation), because in addition to removing any contaminating luciferase associated with the phage, this clean-up may also remove ghost particles (particles that have lost DNA). The ghost particles can lyse bacterial cells via "lysis from without," killing the cells prematurely and thereby preventing generation of indicator signal. Electron microscopy demonstrates that a crude phage lysate (i.e., before cesium chloride clean-up) may have greater than 50% ghosts. These ghost particles may contribute to premature death of the microorganism through the action of many phage particles puncturing the cell membrane. Thus ghost particles may have contributed to previous problems where high PFU concentrations were reported to be detrimental. Moreover, a very clean phage prep allows the assay to be performed with no wash steps, which makes the assay possible to perform without an initial concentration step. Some embodiments do include an initial concentration step, and in some embodiments this concentration step allows a shorter enrichment incubation time.

Some embodiments of testing methods may further include confirmatory assays. A variety of assays are known in the art for confirming an initial result, usually at a later point in time. For example, the samples can be cultured (e.g., CHROMAGAR®, DYNABEADS® assay as described in the Examples, PCR can be utilized to confirm the presence of the microbial DNA, or other confirmatory assays can be used to confirm the initial result.

In certain embodiments, the methods of the present invention combine the use of a binding agent (e.g., antibody) to purify and/or concentrate a microorganism of interest such as *Listeria* spp. from the sample in addition to detection with an infectious agent. For example, in certain embodiments, the present invention comprises a method for detecting a microorganism of interest in a sample comprising the steps of: capturing the microorganism from the sample on a prior support using a capture antibody specific to the microorganism of interest such as *Listeria* spp.; incubating the sample with a recombinant bacteriophage that infects *Listeria* spp. wherein the recombinant bacteriophage comprises an indicator gene inserted into a late gene region of the bacteriophage such that expression of the indicator gene during bacteriophage replication following infection of host bacteria results in a soluble indicator protein product; and detecting the indicator protein product, wherein positive detection of the indicator protein product indicates that *Listeria* spp. is present in the sample.

In some embodiments synthetic phage are designed to optimize desirable traits for use in pathogen detection assays. In some embodiments, bioinformatics and previous analyses of genetic modifications are employed to optimize desirable traits. For example, in some embodiments, the genes encoding phage tail proteins can be optimized to recognize and bind to particular species of bacteria. In other embodiments the genes encoding phage tail proteins can be optimized to recognize and bind to an entire genus of bacteria, or a particular group of species within a genus. In this way, the phage can be optimized to detect broader or narrower groups of pathogens. In some embodiments, the synthetic phage may be designed to improve expression of the reporter gene. Additionally and/or alternatively, in some instances, the synthetic phage may be designed to increase the burst size of the phage to improve detection.

In some embodiments, the stability of the phage may be optimized to improve shelf-life. For example, enzybiotic solubility may be increased in order to increase subsequent phage stability. Additionally and/or alternatively phage thermostability may be optimized. Thermostable phage better preserve functional activity during storage thereby increasing shelf-life. Thus, in some embodiments, the thermostability and/or pH tolerance may be optimized.

In some embodiments the genetically modified phage or the synthetically derived phage comprises a detectable indicator. In some embodiments the indicator is a luciferase. In some embodiments the phage genome comprises an indicator gene (e.g., a luciferase gene or another gene encoding a detectable indicator).

EXAMPLES

Example 1. *Listeria* Phage Evolution to Recognize 3A Serotype of *Listeria monocytogenes*

Passage #1: In one example of phage evolution a mixture of 19115 (serotype 4b)/51782 (serotype 3a) *Listeria mono-* cytogenes was prepared in the following ratios (% Host/Target: 100/0, 90/10, 50/50, 10/90, and 0/100) in 2 mL Brain Heart Infusion (BHI) with 1 mM CaCl2 (5 tubes total—one set for each phage).

Phage were added to each tube individually at an MOI of 1.0. Tubes were incubated with shaking at 30° C. overnight. Tubes were spun down and the supernatant (phage lysate) was filtered through 0.45 μm filter.

All phage lysates (from all host/target ratio tubes) were pooled and plated for single plaques on host and target strains. Plaque lysates were prepared from plaques that were formed on target strain by picking plaque with pipette tip and adding to Luria Broth (LB) MOPS buffer. Plaque lysates were plated for single plaques on host and target strains. These steps were repeated at least 4 times total to isolate mutant phage.

Passages #2-#3" The phage lysate (250 μL) from step 4 above was added to 4 mL of BHI with 1 mM CaCl2. Phage lysates were incubated with shaking (~160 rpm) at 30° C. for 10 hours. Tubes were centrifuged and filtered supernatant (phage lysate) through 0.45 um filter. Phage lysates were plated for single plaques on host and target strains.

Plaque lysates were prepared from plaques that were formed on target strain by picking plaque with pipette tip and adding to Luria Broth (LB) MOPS buffer. Plaque lysates were plated for single plaques on host and target strains. These steps were repeated at least 4 times total to isolate mutant phage.

If no plaques were seen on target strain with first two passages, all steps were repeated.

We claim:

1. A method of producing a mutant phage with expanded host range, comprising:
- (i) preparing a plurality of co-culture mixtures of varying ratios, comprising a host bacterial strain and a target-host bacterial strain;
- (ii) adding a phage strain to each of the plurality of the co-culture mixtures;
- (iii) incubating the plurality of the co-culture mixtures and the phage strain under bacterial culture conditions;
- (iv) collecting a phage lysate from each of the plurality of the co-culture mixtures;
- (v) pooling the collected phage lysates from each of the plurality of the co-culture mixtures;
- (vi) assaying the pooled phage lysates to determine if host phage of the phage strain has expanded; and,
- (vii) isolating the mutant phage with expanded host range, wherein the mutant bacteriophage with expanded host range is a recombinant mutant bacteriophage with expanded host range comprising an indicator gene inserted into a late gene region of genome.

2. The method of claim 1, wherein the recombinant bacteriophage with expanded host range is derived from wild-type A511, P100, LMA4 or LMA8 bacteriophage.

3. The method of claim 1, wherein the indicator gene is codon-optimized and encodes a soluble protein product that generates an intrinsic signal or a soluble enzyme that generates signal upon reaction with a substrate.

4. The method of claim 1, wherein the recombinant bacteriophage with expanded host range further comprises an untranslated region upstream of the indicator gene, wherein the untranslated region includes a bacteriophage late gene promoter and a ribosomal entry site.

5. The method of claim 1, wherein the indicator gene is codon optimized.

6. A method of producing a mutant phage with expanded host range, comprising:
- (i) preparing a plurality of co-culture mixtures of varying ratios, comprising a host bacterial strain and a target-host bacterial strain;
- (ii) adding a phage strain to each of the plurality of the co-culture mixtures;
- (iii) incubating the plurality of the co-culture mixtures and the phage strain under bacterial culture conditions;
- (iv) collecting a phage lysate from each of the plurality of the co-culture mixtures;
- (v) pooling the collected phage lysates from each of the plurality of the co-culture mixtures:
- (vi) assaying the pooled phage lysates to determine if host phage of the phage strain has expanded; and,
- (vii) isolating the mutant phage with expanded host range, wherein the mutant phage with expanded host range is capable of infecting multiple serotypes of *Listeria monocytogenes*.

7. A method of producing a mutant phage with expanded host range, comprising:
- (i) preparing a plurality of co-culture mixtures of varying ratios, comprising a host bacterial strain and a target-host bacterial strain;
- (ii) adding a phage strain to each of the plurality of the co-culture mixtures;
- (iii) incubating the plurality of the co-culture mixtures and the phage strain under bacterial culture conditions;
- (iv) collecting a phage lysate from each of the plurality of the co-culture mixtures;
- (v) pooling the collected phage lysates from each of the plurality of the co-culture mixtures;
- (vi) assaying the pooled phage lysates to determine if host phage of the phage strain has expanded; and,
- (vii) isolating the mutant phage with expanded host range, wherein the phage strain in step (ii) is a bacteriophage of Caudovirales order.

8. The method of claim 7, wherein the bacteriophage of Caudovirales order is a member of Siphoviridae or Helleviridae.

9. The method of claim 1, wherein the phage strain in step (ii) infects the host bacterial strain and not the target-host bacterial strain.

10. The method of claim 1, wherein the host bacterial strain is *Listeria monocytogenes* 19115.

11. The method of claim 1, wherein the target-host bacterial strain is *Listeria monocytogenes* 51782.

12. The method of claim 1, wherein the phage strain in step (ii) is a bacteriophage of Caudovirales order.

13. The method of claim 1, wherein the bacteriophage of Caudovirales order is a member of Siphoviridae or Helleviridae.

14. The method of claim 1, wherein the mutant phage with expanded host range is capable of infecting multiple species of *Listeria*.

15. The method of claim 1, wherein the mutant phage with expanded host range is capable of infecting multiple serotypes of *Listeria monocytogenes*.

16. The method of claim 1, wherein the mutant phage with expanded host range is capable of infecting one or more pathogenic serotypes of *Listeria monocytogenes* and unable to infect non-pathogenic serotypes of *Listeria monocytogenes*.

17. The method of claim 6, wherein the recombinant bacteriophage with expanded host range is derived from wild-type A511, P100, LMA4 or LMA8 bacteriophage.

18. The method of claim 6, wherein the phage strain in step (ii) is a bacteriophage of Caudovirales order.

19. The method of claim 18, wherein the bacteriophage of Caudovirales order is a member of Siphoviridae or Helleviridae.

20. The method of claim 6, wherein the phage strain in step (ii) infects the host bacterial strain and not the target-host bacterial strain.

21. The method of claim 6, wherein the host bacterial strain is *Listeria monocytogenes* 19115.

22. The method of claim 6, wherein the target-host bacterial strain is *Listeria monocytogenes* 51782.

23. The method of claim 6, wherein the mutant phage with expanded host range is capable of infecting one or more pathogenic serotypes of *Listeria monocytogenes* and unable to infect non-pathogenic serotypes of *Listeria monocytogenes.*

24. The method of claim 7, wherein the recombinant bacteriophage with expanded host range is derived from wild-type A511, P100, LMA4 or LMA8 bacteriophage.

25. The method of claim 7, wherein the phage strain in step (ii) infects the host bacterial strain and not the target-host bacterial strain.

26. The method of claim 7, wherein the host bacterial strain is *Listeria monocytogenes* 19115.

27. The method of claim 7, wherein the target-host bacterial strain is *Listeria monocytogenes* 51782.

28. The method of claim 7, The method of claim 1, wherein the mutant phage with expanded host range is capable of infecting multiple species of *Listeria.*

29. The method of claim 7, wherein the mutant phage with expanded host range is capable of infecting one or more pathogenic serotypes of *Listeria monocytogenes* and unable to infect non-pathogenic serotypes of *Listeria monocytogenes.*

* * * * *